(12) United States Patent
Wu et al.

(10) Patent No.: US 9,377,440 B2
(45) Date of Patent: Jun. 28, 2016

(54) METHOD AND APPARATUS FOR PRECISE SELECTION AND EXTRACTION OF A FOCUSED COMPONENT IN ISOELECTRIC FOCUSING PERFORMED IN MICRO-CHANNELS

(71) Applicant: ProteinSimple, Santa Clara, CA (US)

(72) Inventors: Jiaqi Wu, Woodbridge (CA); Tiemin Huang, Waterloo (CA); Arthur H. Watson, Toronto (CA)

(73) Assignee: ProteinSimple, Santa Clara, CA (US)

( * ) Notice: Subject to any disclaimer, the term of this patent is extended or adjusted under 35 U.S.C. 154(b) by 0 days.

(21) Appl. No.: 13/573,799

(22) Filed: Oct. 3, 2012

(65) Prior Publication Data

US 2014/0021053 A1    Jan. 23, 2014

Related U.S. Application Data

(63) Continuation of application No. 11/827,098, filed on Jul. 10, 2007, now abandoned.

(60) Provisional application No. 60/819,390, filed on Jul. 10, 2006.

(51) Int. Cl.
  *G01N 27/447*    (2006.01)
  *G01N 1/40*      (2006.01)
  *B01L 3/00*      (2006.01)

(52) U.S. Cl.
  CPC ............ *G01N 27/44795* (2013.01); *G01N 1/40* (2013.01); *G01N 27/44739* (2013.01); *B01L 3/5027* (2013.01); *G01N 2001/4038* (2013.01)

(58) Field of Classification Search
  CPC .................. G01N 27/44795; G01N 27/44717; G01N 27/44739; G01N 1/40; G01N 2001/4038
  USPC .......................... 204/451, 453, 601–604, 612
  See application file for complete search history.

(56) References Cited

U.S. PATENT DOCUMENTS

| | | |
|---|---|---|
| 2,509,399 A | 5/1950 | Resek |
| 5,228,960 A | 7/1993 | Liu et al. |
| 5,627,643 A | 5/1997 | Birnbaum et al. |
| 5,882,864 A | 3/1999 | An et al. |
| 5,932,080 A | 8/1999 | Likuski |
| 5,963,456 A | 10/1999 | Klein et al. |
| 5,985,121 A | 11/1999 | Wu et al. |

(Continued)

OTHER PUBLICATIONS

Khandurina, J. et al., "Micromachined capillary cross-connector for high-precision fraction collection," Journal of Chromatography A, 979:105-113 (2002).

(Continued)

*Primary Examiner* — Susan D Leong
(74) *Attorney, Agent, or Firm* — Cooley LLP

(57) ABSTRACT

An apparatus and method are disclosed for the precise selection and extraction of a selected analyte in a focused zone produced by isoelectric focusing performed in micro-channels. A cross-channel microfluidic device comprises a sample mixture introduction and separation channel and an extraction channel, which are in fluid communication with each other at a point of intersection. Means are provided for selectively moving the pattern of separated zones following cIEF to the intersection point, and means are provided for applying an extraction pressure to direct a single zone containing a selected analyte into and then out of the extraction channel for collection.

18 Claims, 8 Drawing Sheets

(56) References Cited

U.S. PATENT DOCUMENTS

| | | | |
|---|---|---|---|
| 6,208,941 B1 | 3/2001 | Marks | |
| 6,849,396 B2 | 2/2005 | Schneider | |
| 6,852,206 B2 | 2/2005 | Pawliszyn et al. | |
| 2002/0025576 A1* | 2/2002 | Northrup et al. | 435/288.5 |
| 2004/0168917 A1 | 9/2004 | Tabuchi et al. | |
| 2004/0224362 A1 | 11/2004 | Gjerde et al. | |
| 2005/0155861 A1 | 7/2005 | Guzman | |
| 2006/0254914 A1 | 11/2006 | Biron et al. | |
| 2008/0035484 A1 | 2/2008 | Wu et al. | |
| 2009/0194419 A1 | 8/2009 | Huang et al. | |
| 2010/0155241 A1 | 6/2010 | Ross et al. | |

OTHER PUBLICATIONS

Khandurina, J. et al., "Micropreparative Fraction Collection in Microfluidic Devices," Anal. Chem., 74:1737-1740 (2002).

Kaniansky, D. et al., "Capillary Electrophoresis Separations on a Planar Chip with the Column-Coupling Configuration of the Separation Channels," Anal. Chem., 72:3596-3604 (2000).

Herr, A. E., et al., "On-Chip Coupling of Isoelectric Focusing and Free Solution Electrophoresis for Multidimensional Separations," Anal. Chem., 75(5):1180-1187 (2003).

Muller, O. et al., "Design of a High-Precision Fraction Collector for Capillary Electrophoresis," Anal. Chem., 67:2974-2980 (1995).

Pritchett, T. J.: "Review: Capillary isoelectric focusing of proteins," Electrophoresis, 17:1195-1201 (1996).

Rocklin, R. D. et al., "A Microfabricated Fluidic Device for Performing Two-Dimensional liquid-Phase Separations," Anal. Chem., 72:5244-5249 (2000).

Office Action for U.S. Appl. No. 12/358,724, mailed Oct. 14, 2011.
Office Action for U.S. Appl. No. 12/358,724, mailed Aug. 29, 2012.
Office Action for U.S. Appl. No. 12/358,724, mailed Jul. 1, 2013.
Office Action for U.S. Appl. No. 11/827,098, mailed Apr. 3, 2012.
Office Action for U.S. Appl. No. 11/827,098, mailed Nov. 1, 2010.
Office Action for U.S. Appl. No. 11/827,098, mailed Apr. 20, 2010.

\* cited by examiner

METHOD AND APPARATUS FOR PRECISE SELECTION AND EXTRACTION OF A FOCUSED COMPONENT IN ISOELECTRIC FOCUSING PERFORMED IN MICRO-CHANNELS

CROSS-REFERENCE TO RELATED APPLICATIONS

This application is a continuation of U.S. patent application Ser. No. 11/827,098, filed Jul. 10, 2007, which claims the benefit under 35 U.S.C. §119(e) of U.S. Provisional Patent Application No. 60/819,390, filed on Jul. 10, 2006, the disclosure of which is incorporated by reference herein.

STATEMENT REGARDING FEDERALLY SPONSORED RESEARCH OR DEVELOPMENT

N/A

FIELD OF THE INVENTION

This invention relates to the separation and precise selection and extraction of components of an analyte mixture by means of liquid-phase capillary or micro-channel electrophoresis. The principal application of the invention is to facilitate the identification and characterization of the extracted component(s) through the subsequent use of microanalytical techniques such as mass spectrometry.

BACKGROUND OF THE INVENTION

Capillary electrophoresis (CE) has been established as an important separation technique in bioanalytical chemistry. Separation and detection of very small amounts of biological samples, about pL-nL volumes, can be achieved with CE. This is generally not possible with more conventional separatory methods, even high-performance liquid chromatography (HPLC). There are several CE separation modes in use for different kinds of samples. They include capillary zone electrophoresis, moving boundary capillary electrophoresis, capillary isotachophoresis and capillary isoelectric focusing (cIEF).

CE provides high-resolution and high efficiency separation and is used in proteomic research and biopharmaceutical applications. Not only proven as a powerful analytical tool, CE is also promising for application in nano and micro-fractionation collection. For instance, on-line coupling of CE with mass spectrometry (MS) is used to elucidate protein structure, and off-line CE fractionation collection is important for further characterization of proteins in connection with sequencing, peptide digesting and mapping and reaction studies.

Various designs of microfluidic apparatus have been used for CE fraction collection. Vial collection and membrane collection of individual components of an analyte at the exit of the separation column, with or without the help of sheath fluid, has been investigated. In point-detection capillary electrophoresis, sample fractions are collected from the outlet of the separation channel after passing the detection window. Karger et al. [1] further developed vial collection to a fraction collector. As CE is normally run with 25 to 75 μm i.d. capillaries or micro-channels, extremely small volumes of individual fractions can be expected. Therefore, exact timing is important for precise fractionation. Cross-contamination frequently occurs for closely migrating peaks due to the extremely narrow peak width and extremely small amount of eluant.

An important CE mode, capillary isoelectric focusing (cIEF), is used for separating amphoteric substances such as peptides and proteins in a capillary or micro-channel under an electric field. Across the separation capillary or channel, voltage is applied and a pH gradient is created by carrier ampholytes that have been pre-mixed with the analyte sample, acidic at the anodic end of the channel and alkaline at the cathodic end of the channel. Each component in the analyte mixture migrates to a position in the separation channel where the surrounding pH corresponds to its isoelectric point. Therein, as zwitterions possessing no net charge, molecules of that component cease to move in the electric field. Different amphoteric components are thereby focused into narrow, stationary zones.

cIEF is the highest resolution CE mode for charge-based separation of amphoteric substances such as proteins and peptides. It has most often been used to separate closely related proteins having subtle differences between their structures. In the cIEF separation channel, components of the analyte mixture, which evenly distribute along the whole channel before the separation process, are separated and focused into narrow, stationary, component zones.

Uniquely narrow zones are formed using cIEF because: 1) zone broadening due to parabolic flow is not a factor in the separation process; 2) the focusing force is reverse to diffusion and 3) the electrophoresis current during focusing is low compared to other CE modes thus minimizing the effects of component zone broadening due to Joule heating. For these reasons, the analyte components from cIEF are concentrated over a hundredfold in their separated, narrow zones.

In column or micro-channel separation technologies, the narrower the component zone is the higher the resolution. Narrow zones in other CE modes can be achieved by injecting a very small 'analyte plug' representing a very small segment of the whole separation channel. Even then, however, component zone broadening is unavoidable during the separation process for the reasons stated above. By contrast, cIEF allows the whole separation channel to be filled with the analyte sample mixture without any deterioration of the separation resolution. In comparison to other CE modes, this provides cIEF with a much higher analyte loading capacity.

The absence of parabolic flow broadening with static, focused zones and low electropheresis current makes cIEF's separation resolution much less dependent on small dimensional separation channels. The separation channel's cross-sectional dimension can be 2 to 5 times larger than other CE modes with comparable separation resolution. Use of a larger cross-sectional separation channel again further increases sample analyte loading capacity. Higher sample loading provides a higher amount of extracted component material. Increasing the amount of extracted material is highly desirable since it generally increases the analytical success of subsequent analytical techniques such as mass spectrometry.

For the foregoing reasons, cIEF would appear to be an attractive technique for nano/micro preparative fractionation of closely related proteins from a mixture, for example, variants of hemoglobin arising from mutations to the amino acids sequences; or different forms of recombinant proteins arising from the heterogeneity associated with different post-translational modifications.

Others have investigated the use of cIEF for fraction collection, as an aspect of CE fractionation generally. For example, Guttman et al [4,5] have studied "planar" electrophoresis using a capillary cross-connector. By applying different voltage configurations through different reservoirs, a component zone or peak was collected after passing a single-point detector.

To date, however, others have had limited success in achieving any high degree of precision in the selection and extraction of cIEF component zones, chiefly because of the following limitations to the operation of their devices: 1) mobilization flow is in one direction; 2) mobilization speed is pre-determined and generally fixed and 3) inability to visualize the entire separation zones and detect in real-time any zone-width distortion due to mobilization.

In conventional "single point on-column" detection cIEF, the focused zones or peaks within the capillary must be moved, chemically or electroosmotically, past the detection point to be detected. This mobilization step in cIEF requires extra time and distorts the focused peaks, making it difficult to collect pure peaks without cross-contamination when peaks focus in close proximity.

It has, accordingly, not been possible with existing microfluidic (capillary) electrophoretic devices for micro-preparative fraction collection to observe all of the separated peaks developed by electrophoresis, then select a particular peak of interest and mobilize the entire pattern of peaks, while maintaining or re-establishing the focus of the pattern to bring the selected peak to a separation/collection point.

It is a principal object of the current invention to provide an integrated micro-scale electrophoresis device (IMED) for the extraction of large (μg) or small (ng) amounts of components (in particular, proteins) separated by cIEF.

It is a particular object of the invention to provide such an IMED as aforesaid which is adapted for automatic sample injection and capable of high-resolution protein separation, selection of a specific protein zone or peak and precision extraction of the central portion of the selected protein peak ("heart-cut extraction") for further characterization.

SUMMARY OF THE INVENTION

In its broadest aspect, the apparatus of the invention is apparatus useful for the selective extraction of an analyte from a mixture of analytes using capillary isoelectric focusing, which includes: a capillary separation channel filled with a medium containing a mixture of ionic components in which target analytes migrate are separated into zones and in stationary or near stationary equilibrium; a capillary extraction channel intersecting with and angularly displaced from said capillary separation channel and in fluid communication therewith at the location of intersection; means for causing selected zones of analytes separated by capillary isoelectric focusing to move to said intersection of the separation and extraction channels in a time-independent manner; optical whole column imaging detection apparatus for monitoring the isoelectric focusing process and observing the position of the separated zones of analyte; and means for applying an extraction force to direct a single zone containing a selected analyte into and then out of extraction channel in a time-independent manner.

According to a preferred embodiment of apparatus according to the invention there is provided a coplanar, cross-channel microfluidic device comprising a sample mixture introduction and separation channel and an extraction channel in fluid communication at a point of intersection; means of producing a pattern of amphoteric components separated into focused, stationary zones within the separation channel; an apparatus for irradiating the whole separation channel with ultraviolet (UV) light and having a detector that can provide UV absorption imaging detection of the whole separation channel providing real-time or at least very, rapid digital images of the cIEF separation process; means of selecting a specific focused, component zone or peak in the separation channel and moving the said peak to the intersection of the separation and extraction channels; the aforementioned whole-channel, real-time imaging detection apparatus to monitor the movement of the selected component peak and to visualize the alignment of said peak to the intersection of the separation and extraction channels; and means for moving the aligned, component peak or a portion of the peak into and then out of the extraction channel for collection or interface to a second analytical apparatus such as a mass spectrometer.

The invention is also directed to a method for fractionating and extracting analytes capable of resolution by capillary isoelectric focusing, comprising the steps of providing a capillary separation channel and a capillary extraction channel in fluid communication therewith; introducing an analyte sample containing a mixture of ionic analytes prepared for electrophoresis into the separation channel; separating and focusing components of the analyte mixture into separated zones in the separation channel using capillary isoelectric focusing; monitoring the process of capillary isoelectric focusing and positions of the separated analyte zones using whole column imaging detection means; causing the separated zones to move selectively to the intersection of the separation and extraction channels; and applying an extraction force to direct a zone containing desired analytes out through the extraction channel for collection.

According to particular embodiments of the method of the invention, the separated zones are caused to move along the separation channel to the intersection of the separation and extraction channels by orienting the separation channels so that gravity causes the desired motion. Microfluidic delivery means may be used to move the separated zones and also to apply the extraction force.

BRIEF DESCRIPTION OF THE DRAWINGS

The invention will now be described further, with reference to the accompanying drawings, in which.

DESCRIPTION OF PREFERRED EMBODIMENT

Figure 1:
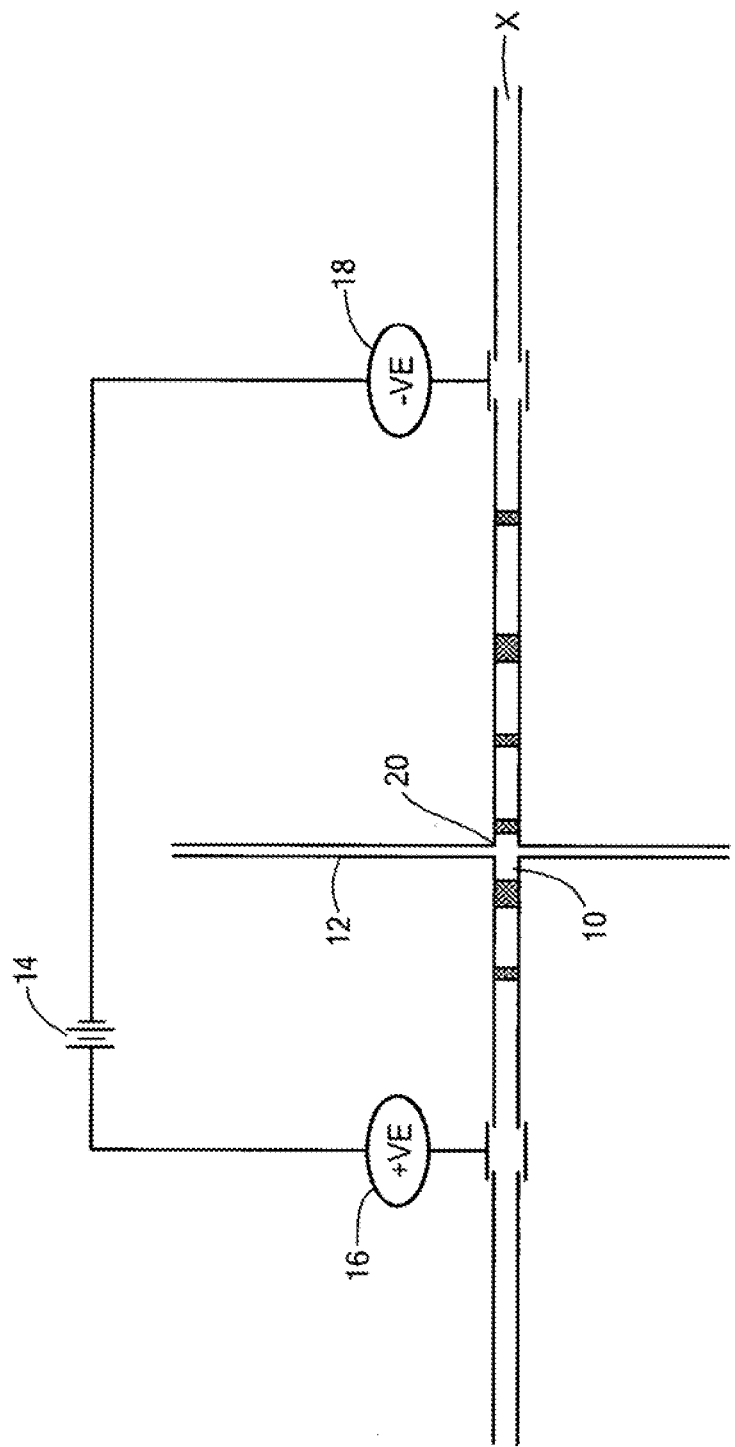
FIG. 1 is a schematic illustration of essential components of an IMED for use in the separation and extraction of sample components according to the present invention.

As illustrated in FIG. 1, an analyte sample containing a mixture of ionic components is prepared for capillary isoelectric focusing (cIEF) electrophoresis and is injected into a separation channel 10 (horizontal in the Figure) in fluid communication with an extraction channel 12 (vertical in the Figure) until it is completely full (overflowing). In the separation channel, components of the sample mixture are separated and focused using cIEF. Channels 10 and 12 may be in the form of a co-planar, monolithic microfluidic device or microchip in which closed, elongate separation and extraction channels have been created. In an alternative arrangement of channels 10 and 12, their locus of intersection and fluid communication may be formed by four pieces of fused silica capillary tubing.

A high voltage power supply 14 is connected to anode 16 and cathode 18 and sets up both a voltage and a pH gradient liquid medium, acidic in the region of anode 16 and alkaline near cathode 18. As noted above, each component in the analyte mixture migrates to a position corresponding to it isoelectric point. Different amphoteric compounds are thereby focused into narrow, stationary zones.

Figure 2:
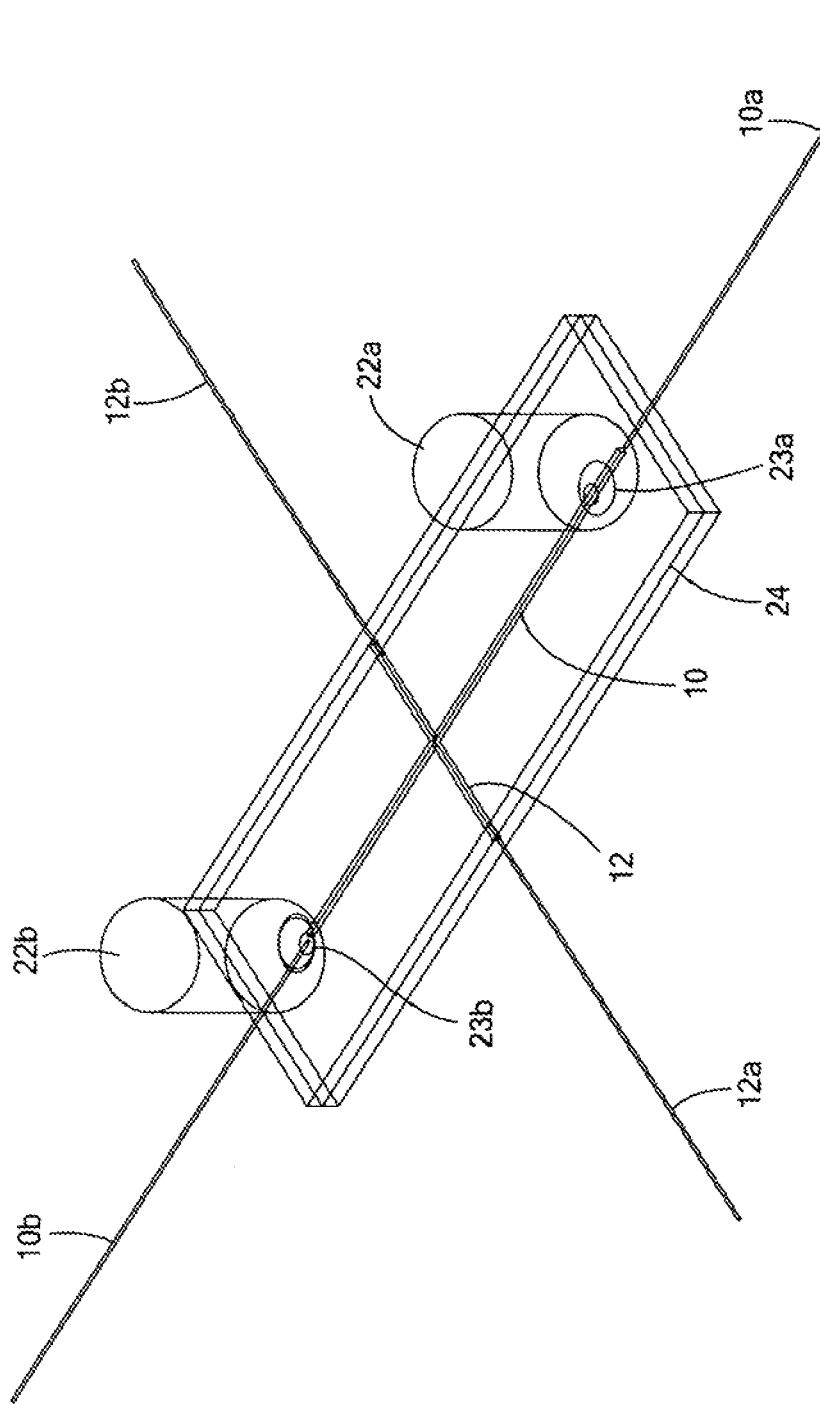
FIG. 2 schematically illustrates an IMED of the same configuration as FIG. 1, but illustrating the arrangement of electrolyte holding tanks and semipermeable membranes used for handling of ampholytes and analyte samples in solution into the IMED.

FIG. 2 is operationally equivalent to the IMED of FIG. 1, but further shows two electrolyte tanks 22a and 22b that are integrated in the IMED to hold anolyte and catholyte. These tanks are connected with the separation channel through semi-permeable membranes 23a and 23b. The semi-permeable membrane, having a thickness of about 10 μm and a pore size less than 10 nm is sandwiched between the separation channel and the electrolyte tank, to permit the application of high level electric fields and to avoid unwanted mixing of the sample with electrolytes in the electrolyte tanks.

In the arrangement of FIG. 2, separation and extraction channels 10 and 12 are formed in a microchip 24 and respectively extend beyond perpendicular edges of the microchip 24 through capillaries 10a/10b and 12a/12b.

When the IMED illustrated in FIG. 2 is used to extract proteins, the entire separation channel is UV transparent to allow whole separation channel UV detection.

According to the invention, the surface properties (e.g., hydrophobicity and surface charge) of at least the separation channel of the IMED are selected with a view to achieving high resolution separation of amphoteric components such as proteins.

An important reason for controlling the surface charge in the separation channel is to minimize electro-osmotic flow. Many plastic substrates such as polycarbonate, Teflon® and PMMA exhibit sufficient transparency to ultraviolet light for the purposes of the invention and develop limited surface charge. With dynamic coating using methyl cellulose (MC), MC derivatives or polyvinyl alcohol, the separation channel surface is unreactive with protein.

If UV transparent fused silica, glass or quartz is employed as the separation channel substrate for the IMED, additional surface modification is necessary to control surface charge. This can be achieved by coating with such polymers as linear or cross-linked polyacrylamide.

As seen in FIG. 2, separation channel 10 is connected with two pieces of capillary 10a and 10b at either end, to allow for the injection of sample and for manipulation of the separated component peaks. Separation channel 10 crosses integrally with extraction channel 12, whose dimension should be no larger than that of the separation channel to allow for "heart cut" extraction of the selected component peak. As with the separation channel 10, extraction channel 12 has two integral capillaries 12a and 12b communicating with either end of extraction channel 20, to allow for peak extraction and collection or interface with a second selected separation/analytical apparatus, such as a mass spectrometer.

Figure 3:
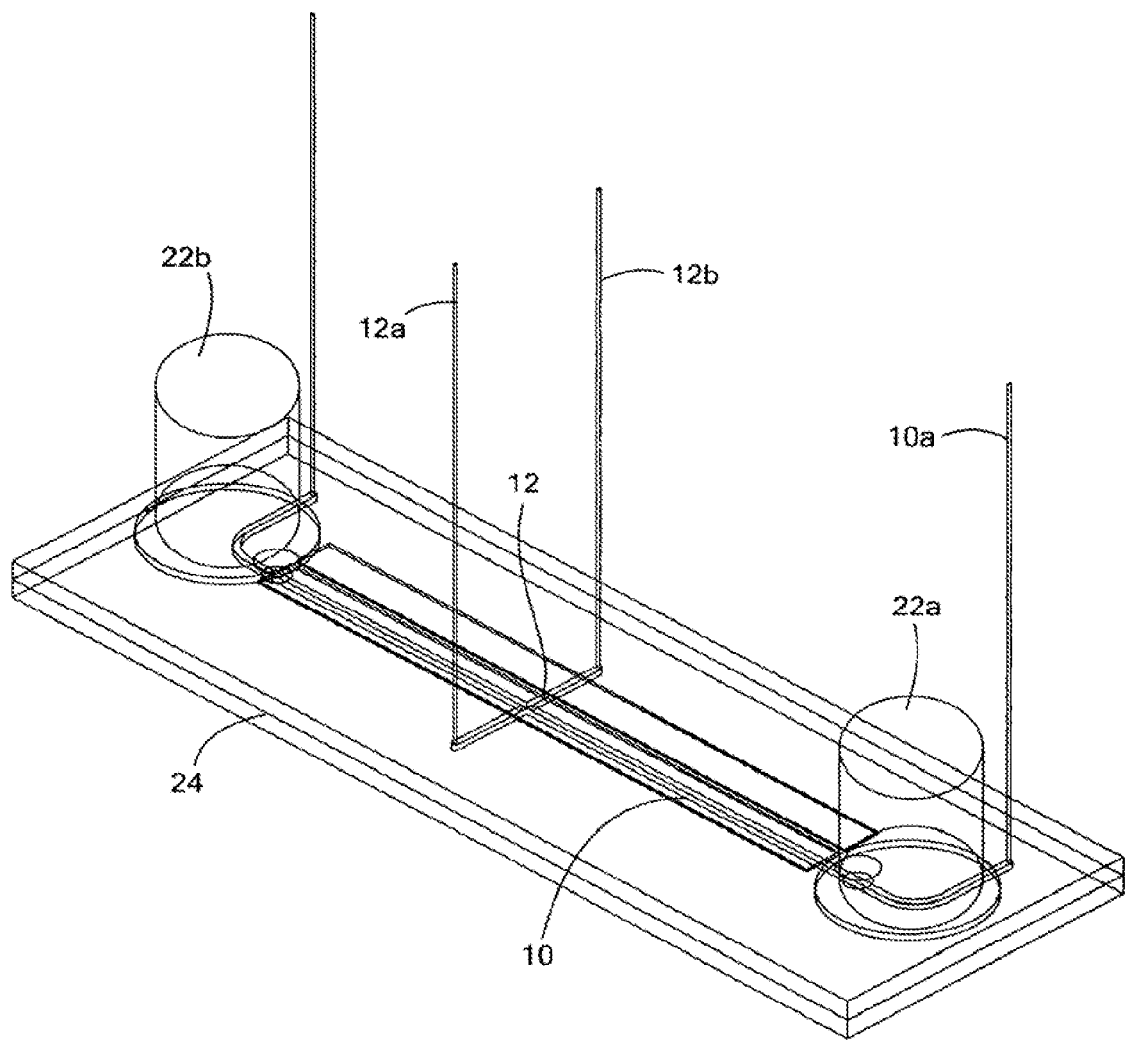
FIG. 3 illustrates a variant of the IMED of FIG. 2, having a different configuration of interconnecting separation and extraction channel capillaries.

FIG. 3 shows an arrangement like that of FIG. 2, but in which capillaries 12a and 12b extend perpendicularly to their associated extraction channel 12 as does extension capillary 10a relative to separation channel 10.

The apparatus of the invention includes a whole column imaging device (WCID) apparatus [not shown in the drawings] to irradiate the whole or at least a large portion of the length of the separation channel with ultraviolet (UV) light or other light. Apparatus of this kind has been described in United States patents of some of the present inventors, particularly U.S. Pat. Nos. 5,784,154 and 6,852,206, whose disclosures are hereby incorporated by reference. The WCID incorporates a detector that provides UV absorption or fluorescent imaging detection of the whole, or at least a large portion, of the length of separation channel. The apparatus is capable of providing real-time or at least very, rapid digital absorbance images of the separation channel and incorporates imaging optics (e.g., lens, CCD) that afford imaging resolutions that exceed the separation resolution of the cIEF method.

During the entire cIEF separation and focusing process, the whole (or near whole) separation channel is monitored using the aforementioned real-time image detection apparatus and the complete component separation pattern within the separation channel is 'visualized'. At any given moment, the precise spatial position and width of each component zone or peak in the separation channel is known.

After the cIEF separation and focusing process is complete, the separated zones or peaks are stationary and remain spatially fixed relative to each other. These focused peaks, as a set, can be moved back and forth (i.e., to the right or to the left within the horizontal separation channel) with extremely fine axial resolution control. For example, axial motion control of a peak can be less than +/−50 um with negligible peak-broadening distortions using a number of ways such as pressure difference. Axial motion control of this accuracy requires real-time (or near-real time) monitoring using the above detection apparatus that visualizes the whole length of the separation channel. Also, the exact spatial position and width of the extraction channel that intersect the separation channel can be determined by the whole-channel detection apparatus.

With particular reference to FIG. 1, separation channel 10 and extraction channel 12, are in fluid communication where they intersect. Before sample mixture introduction, the extraction channel 12 is completely filled (overflowing) with a desired matrix (such as water or a selected pH and ionic strength buffer), and then both ends are sealed or plugged (e.g., with end caps or shut valves). This sealing constrains the matrix within the sample extraction channel and also prevents the mixing of the sample mixture during sample mixture introduction. The separation channel 10 is then completely filled (overflowing) with the analyte sample containing a mixture of ionic components is prepared for cIEF separation. Upon application of an electric field across the separation channel, analyte focusing and separation is conducted within the separation channel, which is visualized or monitored with a real-time, whole-separation channel detection apparatus.

If identification of a particular analyte zone, say Zone A in FIG. 1, is the objective, then all the zones within the separation channel are moved slowly toward the left end of the channel by operation of a pressure differential imposed in the direction X. During this motion, the electrophoresis voltage is kept on to maintain the focused zones. Once again, the real-time whole-channel detection apparatus is used to visualize the motion of the zones or peaks towards the left end of the channel.

The zone or peak pattern can be moved back and forth along the separation channel with very fine motion control by positive or negative pressure. For example, if one end of the horizontal separation capillary is slightly raised or lowered with respect to the other end, the peak pattern will move under the force of gravity. Alternatively, a pressure differential can be created across the separation channel by means of a conventional microfluidic delivering system, in the nature of a pump. The invention also contemplates movement of the peak pattern back and forth by chemical means, e.g. by changing the composition of the anolyte or the catholyte (located in tanks at each end of the separation channel).

Once Zone A is aligned with the extraction channel 12 intersection (e.g., the centerline of Zone A is superimposed over the centerline of the extraction channel) as can be visualized by the real-time, detection apparatus, the imposed lateral movement of Zone A is stopped. This extraction method is time independent and adaptive in nature in that it allows for very fine corrective or adjustment motion in either direction until the selected zone is properly aligned to the extraction channel.

With the selected zone now properly aligned at the intersection of the separation and extraction channels, both ends of the separation channel 10 are sealed or plugged (e.g., with end caps or shutoff valves) and both ends of the extraction channel 12 are unplugged or unsealed. Zone A extraction is performed by applying a controlled pressure difference across the ends of the extraction channel until Zone A is passed into and then out of the extraction channel. Again, the pressure differential may simply be the force of gravity or be established by the pressure impressed across the channel by micro-fluidic delivering system; or, by setting up an electro-osmotic flow—EOF (applying voltage through two microvials at both ends of the extraction channel, with the channel wall modified to generate EOF in the desired direction). In this manner, over short distances, any zone within the separation channel can be selected and precisely extracted.

During zone or peak motion, the real-time, whole-column detection apparatus can monitor and visualize for possible separation resolution disturbances allowing for corrective actions such as halting motion for a period of time to allow for refocusing.

As noted above, others have used cross-channel arrangements for CE. The differences between the apparatus and method of the present invention from previous attempts at separation and fractionation of analytes, which make our invention more precise for the selection and extraction of an analyte, will now be discussed.

The current invention uses a real-time, whole separation channel detector apparatus to visualize the entire separation channel. Since the position of the extraction channel intersection and the position and width of the selected component zone are known or are visualized precisely at any given time and over short distances very fine axial motion control can be made using microgravity differences, the alignment and extraction of the selected zone can be made with high precision and specificity.

The component zones or peaks within the separation channel can be micro-manipulated to move back and forth in the separation channel in cIEF in an essentially time-independent manner, and this permits continuous corrective action until alignment is complete. Combining the static nature of cIEF focused peaks with real-time, whole-column detection makes this method highly selective since any peak in the separation channel can be selected and moved to the position of the extraction channel. In other methods, all sample peaks move in one direction and once a peak is missed, it cannot be moved back.

The method and apparatus of the present invention lends itself to automated peak extraction. The real-time, whole-column detection apparatus displays absorption peaks on a monitor for human interpretation and manipulation for specific peak extraction. However, the electronic signals produced by the real-time, detection apparatus can be interpreted by a peak-find processing software algorithms and then, using real-time data control the selection, alignment and extraction of peak based on user-defined extraction criteria.

This method and apparatus are also amenable to multiple cross-channel separations and extraction channels in a single microchip to assist in automation.

This method and apparatus could be used to integrate multiple extraction channels with a single separation channel. Also, the position of an extraction channel intersection can be preferentially located at a place on the separation channel to optimize extraction of components with certain pI values.

This method and apparatus of the invention produce extraction volumes and concentrations levels well exceeding the minimum requirement for further peak identity analysis of the peak using modern mass spectrometry with ionization techniques such as electrospray and matrix assisted laser desorption ionization (MALDI).

EXPERIMENTAL EXAMPLES

Example 1

An IMED having the structure shown in FIG. 3 was used to selectively extract different hemoglobin variants of a mixture. An imaged cIEF system (Model iCE280, Convergent Bioscience Ltd., Toronto, Canada) was used as the real-time, whole separation channel UV detection apparatus, and protein detection was achieved through UV absorption at 280 nm. An autosampler from Prince CE system (Prince. Technologies, Emmen, The Netherlands) was used for sample injection and fluid manipulation along the separation channel. Methyl cellulose (MC), horse heart myoblobin, human transferrin, and pH 3-10 Pharmalyte were obtained from Sigma (St Louse, Mo.). Hemoglobin control AFSC was obtained from Helena Laboratories (Beaumont, Tex.). HPLC grade water was from J. T. Baker (Phillipsburg, N.J.), and was used for all solutions. Sample mixture solution was prepared by mixing protein with 8% pH 3-10 Pharmalytes and 0.35% MC.

The extraction channel of the IMED was first filled with HPLC water or preferred buffer, and each end of the capillary connected with the extraction channel was sealed with an end cap or shutoff valve. Then, sample mixture solution was injected into the separation channel of the IMED with the autosampler. Anolyte of 80 mM $H_3PO_4$ in 0.1% MC and catholyte of 100 mM NaOH in 0.1% MC were filled into the corresponding electrolyte tank. cIEF was achieved by applying 1.5 kV across the electrolyte reservoirs for about 10 minutes and then maintaining at 3 kV during focusing, peak manipulation, and peak extraction.

Figure 4:
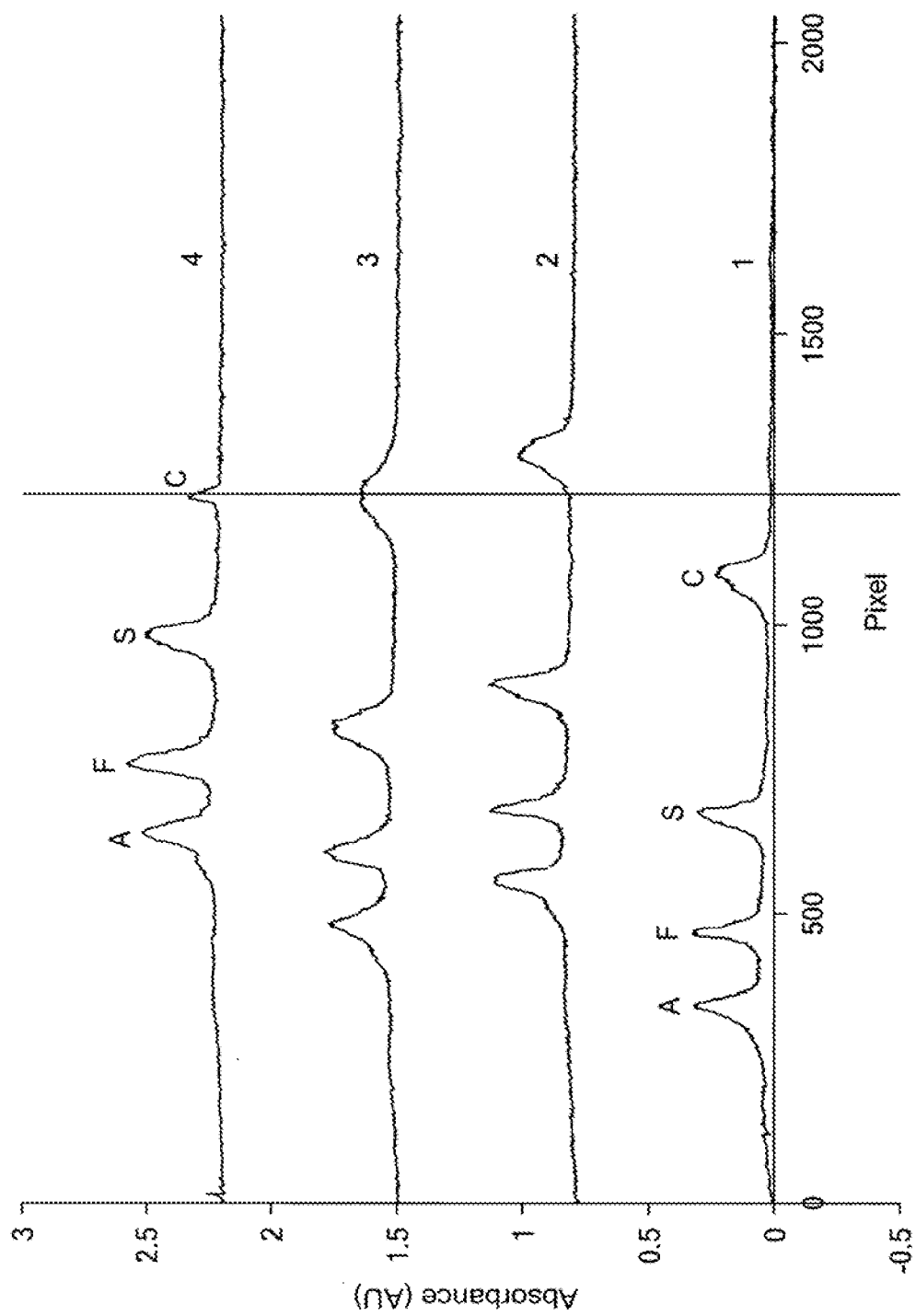
FIG. 4 is a graphical representation (electropherograms) of protein zones as light absorbance peaks along the whole length of the separation channel, illustrating the separation, manipulation and extraction of selected component Hemoglobin C by means of the IMED of FIG. 3.

FIG. 4 illustrates the separation, manipulation, and extraction of Hemoglobin C achieved in this operation of the IMED. The separated protein peaks were monitored with the whole separation channel detector. Trace 1 shows the target components (Hemoglobin C) is located to the left of the extraction cross section (which is indicated with the vertical line in the figure). The separated protein peaks are directed to the right by an imposed pressure differential. Trace 2 shows the target component is to the right of the extraction cross section. Trace 3 illustrates how the target component is manipulated previously to the extraction cross section as desired.

At this stage, both ends of the separation channel were shut off and pressure different was applied to the end of extraction channel to extract Hemoglobin C. Trace 4 shows the refocusing of protein peaks with a heart cut Hemoglobin C extracted. It can be seen that the four major components of Hemoglobin AFSC control are very well separated, while the peak area of Hemoglobin C is significantly reduced.

This example above illustrates the power of the IMED of the invention in manipulating separated protein peaks back and forth along the separation channel to achieve precise heart cut extraction. However, it will seldom be necessary to manipulate a target component back and forth (i.e. in two linear directions) to position the peak cross section for a precise heart cut extraction, since the detector allows real time (images at less than 1 second intervals) monitoring of the manipulation process.

Example 2

Figure 5:
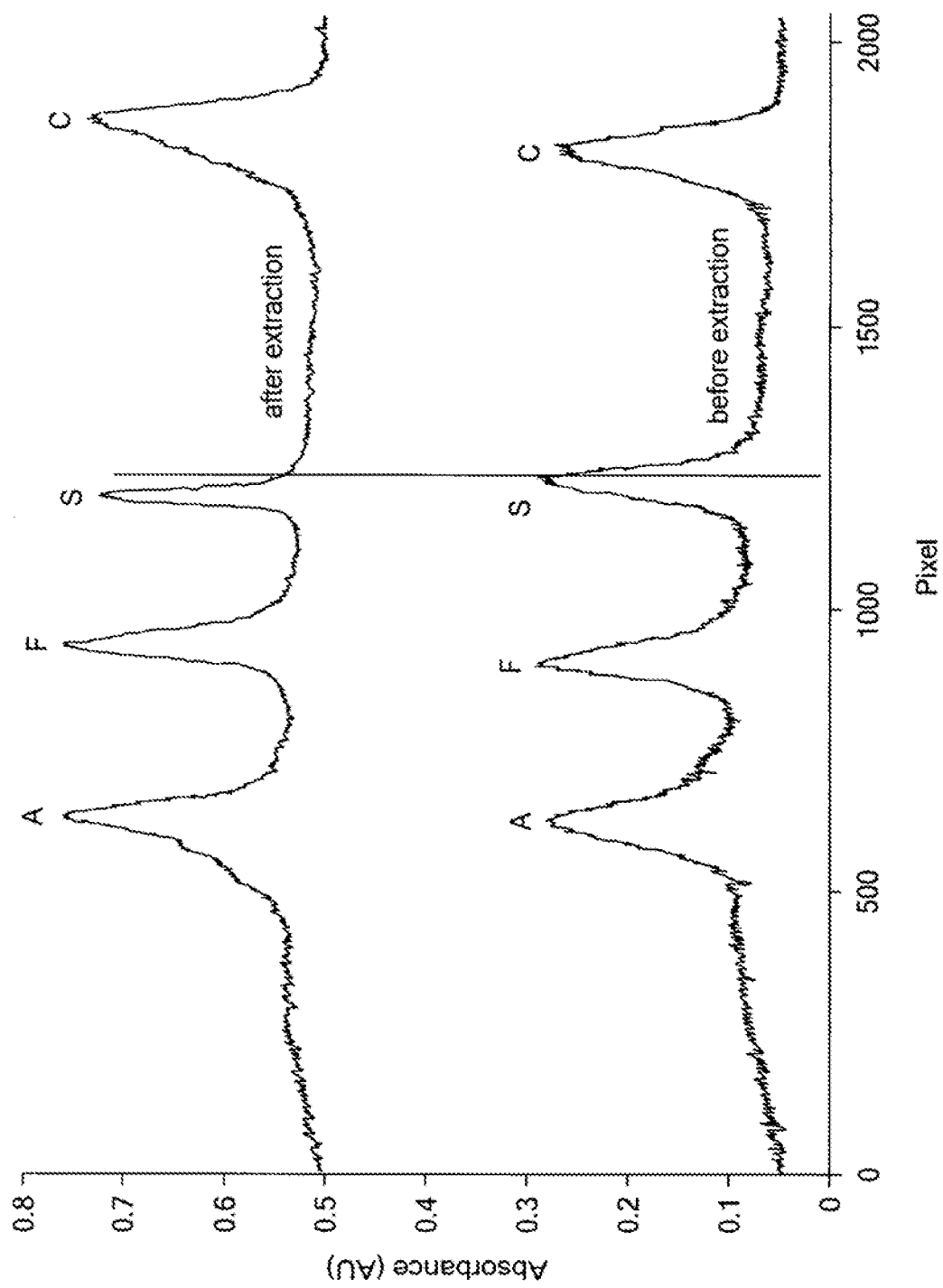
FIG. 5 presents electropherograms of absorbance peaks versus separation channel position showing the separation and extraction of selected component Hemoglobin S in the same IMED as employed to produce the results of FIG. 4.

FIG. 5 shows the separation and extraction of Hemoglobin S in the IMED with the device according to FIG. 4. The pI difference between Hemoglobin F and S and between Hemoglobin S and C was about 0.1. It can be seen that the separation pattern was not affected significantly upon hemoglobin s extraction, while the peak area of Hemoglobin S was reduced following extraction.

Example 3

Figure 6:
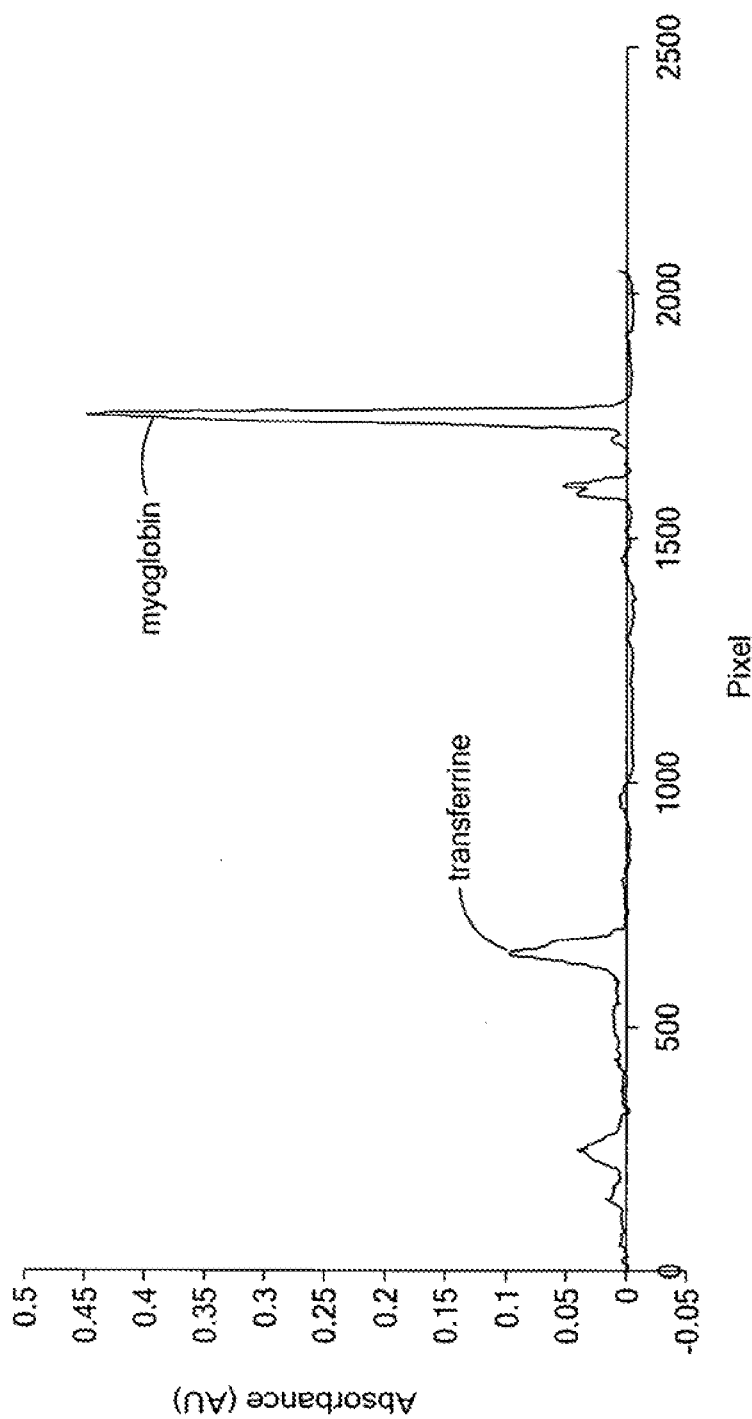
FIG. 6 shows the cIEF electrophoregram of myoglobin and transferrine using an IMED having the structure shown in FIG. 2.

An IMED having the structure substantially represented in FIG. 2 was used to separate and selectively extract target protein component for off line MALDI-TOF characterization. FIG. 6 shows the cIEF electrophoregram of myoglobin and transferrine in 8% 5-8 Pharmalytes, 0.35% MC solution. It can be seen that the major component of transferrine and the major component of myoglobin were very well separated. Upon cIEF separation, the extracted individual protein was diluted to 100 μL in DI water, and 1 μL of this diluted sample was further diluted at either 1:2 or 1:10 ratio with 0.2% (v/v) trifluoroacetic acid in water. The further diluted protein sample of 1 μL was mixed with 1 μL of sinapinic acid (10 mg/mL), and 1 μL of this sample mixture was spotted for MALDI TOF MS (Voyager STR, Applied Biosystems, Foster City, Calif.).

Figure 7:
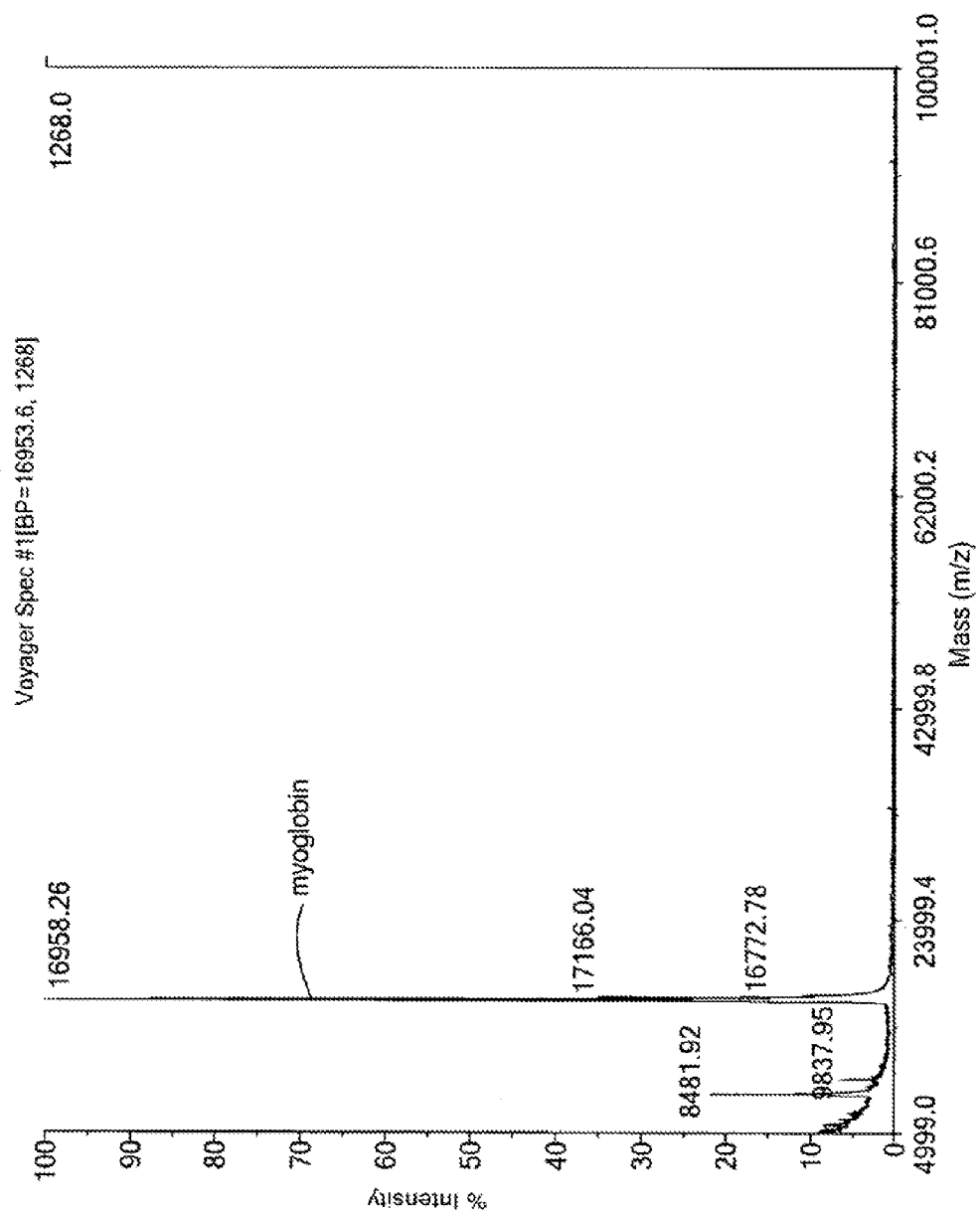
FIG. 7 illustrates the mass spectrogram of separated and extracted myoglobin component from a separation carried out by apparatus of the invention and illustrated in FIG. 3.
Figure 8:
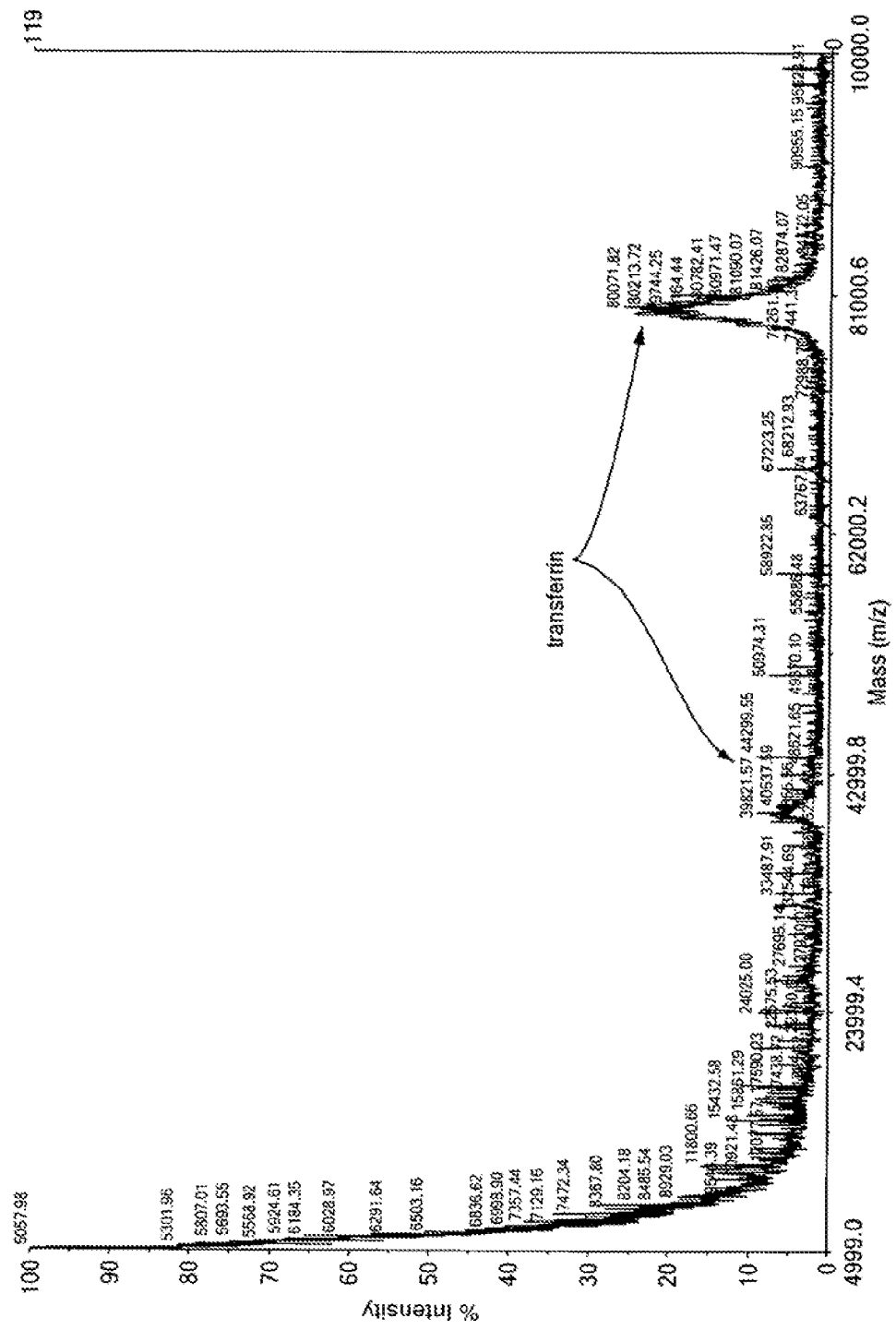
FIG. 8 illustrates the mass spectrogram of separated and extracted transferrine component from the separation carried out by apparatus of FIG. 3.

FIGS. 7 and 8 shows the mass spectrograms of extracted myoglobin and transferrine. From the mass spectrogram, it can be seen that the presence of carrier ampholytes and MC has insignificant impact on the MALDI TOF MS analysis of protein, and the purity of the extracted protein was further confirmed.

The above experimental examples demonstrate that the extracted component in a relatively larger dimension IMED is sufficient for further protein enzyme digestion and mass spectrometer (MS) characterization.

The foregoing description of embodiments of the invention are for illustrative purposes and no limitation of the invention to the specific construction shown and described herein should be inferred. Various modifications apparent to those skilled in the art may be made without departing from the invention defined in the appended claims.

REFERENCES

The disclosure of every reference listed below is hereby incorporated into the present specification by reference.
1. Müller O.; Foret S.; and Karger, B. L. *Anal. Chem.* 1995, 67, 2974-2980
2. Paitchett J. Thomas *Electrophoresis* 1996, 17, 1195-1201
3. Kuhn R.; Hoffsterrer-Kuhn S. *Capillary Electrophoresis Principles and Practice*, Springer Laboratory, Berlin Heidelberg, Germany, 1993
4. Khandurina J.; Guttman A. *Journal of Chromatography A*, 979 (2002) 105-113
5. Khandurina J.; Chovain T.; Guttman A. *Anal. Chem.* 2002 74, 1737-1740
6. Herr, Amy E; Molho, Joshua I; etc *Anal. Chem.* 2003, 75, 1180-1187
7. Kniansky, Dusan; Masar, Marian; *Anal. Chem.* 2000, 72, 3596-3604
8. Rocklin, Roy; Ramsey, Roswitha S; Ramsey, J. Micheal *Anal. Chem.* 2000, 72, 5244-5249

We claim:

1. An apparatus for the precise selection and extraction of an analyte from a mixture of ionic analytes separated by capillary isoelectric focusing, comprising:

a separation channel including a sample inlet end and an outlet end;

a first electrolyte holder that is disposed at the sample inlet end and that is in fluid communication with the separation channel through a first semi-permeable membrane;

a second electrolyte holder that is disposed at the outlet end and that is in fluid communication with the separation channel through a second semi-permeable membrane;

a high-voltage power supply for applying an electric field across the separation channel for analyte focusing and analyte separation and further adapted to create in said separation channel a pH gradient liquid medium that is acidic or substantially acidic at one of the sample inlet end and the outlet end and alkaline or substantially alkaline at another of said sample inlet end and said outlet end;

an extraction channel angularly displaced from said separation channel and in fluid communication therewith at a location of intersection and having an extraction outlet end and an inlet end;

means for filling the separation channel with a mixture of ionic analytes and for causing different analytes to separate and focus into stationary or near stationary zones by capillary isoelectric focusing electrophoresis;

means for selectively causing a selected analyte zone of the analyte zones separated by capillary isoelectric focusing to move to said intersection of the separation and extraction channels in a time-independent manner based on data associated with a real-time image of the whole separation channel;

an optical image detection apparatus including a light source for irradiation of the whole separation channel with ultraviolet (UV) light or other light and capable of acquiring and monitoring in real-time, or at least very rapid time, digital images of ultraviolet absorption or fluorescence detection of focused analyte zones simultaneously in the whole separation channel; and means for applying an extraction force to direct the selected analyte zone or a portion thereof into and then out of the extraction channel for collection or interface to a second analytical apparatus.

2. The apparatus of claim 1, wherein the apparatus is configured to be used to perform a method for precise selection and extraction of an analyte from a mixture of ionic analytes separated by capillary isoelectric focusing, the method comprising the steps of:
filling to overflow the extraction channel with a matrix buffer such as water or a selected pH and ionic strength buffer and then sealing the ends of the extraction channel;
filling to overflow the separation channel with a sample containing a mixture of ionic analytes prepared for isoelectric focusing electrophoresis;
separating and focusing components of the analyte mixture into discrete zones in the separation channel using capillary isoelectric focusing;
monitoring in real-time the process of capillary isoelectric focusing and positions of the separated analyte zones until the focusing is complete and focused zones are stationary or near stationary, using whole separation channel imaging detection;
monitoring in real-time the positions of the separated analyte zones, selecting an analyte zone, and causing said selected analyte zone to move and precisely align with the intersection of the separation and extraction channels and detecting said alignment;
sealing the ends of the separation channel; and
unsealing the ends of the extraction channel and applying an extraction force to direct the selected analyte zone or a portion thereof into and then out of the extraction channel for collection or interface to a second analytical apparatus.

3. The apparatus of claim 1, wherein said intersecting separation channel and extraction channel are formed of a coplanar, monolithic microfluidic device or microchip having closed, elongate separation and extraction channels.

4. The apparatus of claim 3, wherein the microfluidic device or microchip is made of a UV transparent plastic.

5. The apparatus of claim 4, wherein the said UV-transparent plastic is selected from the group consisting of polycarbonates, polyfluorinated polyethylene and polyethylmethacrylate.

6. The apparatus of claim 3, wherein said microfluidic device or microchip is made of quartz or fused silica in which the walls of said separation and extraction channels have been coated with linear or cross-linked polyacrylamide.

7. The apparatus of claim 3, wherein said intersecting separation channel and extraction channel are formed of four pieces of silica, glass or quartz tubing coated with linear or cross-linked polyacrylamide.

8. The apparatus of claim 1, wherein said means for causing a selected analyte zone of the analytes zones separated by capillary isoelectric focusing to move to the intersection of the separation and extraction channels in a time independent manner is made by raising or lowering one end of the separation channel (inlet end or outlet end) relative to the other end thereby causing the zone to move under the force of gravity.

9. The apparatus of claim 1, wherein said means for causing a selected analyte zone of the analytes zones separated by capillary isoelectric focusing to move to the intersection of the separation and extraction channels in a time-independent manner is made by a pressure difference impressed across the separation channel by means of a microfluidic delivery system.

10. The apparatus of claim 1, wherein said means for causing a selected analyte zone of the analytes zones separated by capillary isoelectric focusing to move to the intersection of the separation and extraction channels in a time-independent manner is made by chemical means by changing the composition of the analyte or catholyte found at either end of the separation channel.

11. The apparatus of claim 1, wherein said means for applying an extraction force to direct the selected analyte zone or a portion thereof into and then out of the extraction channel is made by raising or lowering one end of the extraction channel (inlet or outlet end) relative to the other end thereby causing the zone to move into the extraction channel under the force of gravity.

12. The apparatus of claim 1, wherein said means for applying an extraction force to direct the selected analyte zone or a portion thereof into and then out of the extraction channel is made by a pressure difference impressed across the extraction channel by means of a microfluidic delivery system.

13. The apparatus of claim 1, wherein said means for applying an extraction force to direct the selected analyte zone or a portion thereof into and then out of the extraction channel is made by setting up an electro-osmotic flow (EOF) through an application of voltage across microvials located at each end of the extraction channel.

14. The apparatus of claim 1, wherein multiple cross-channel separation and extraction flow paths are formed from a single co-planar, monolithic microfluidic device or microchip.

15. The apparatus of claim 1, wherein multiple extraction channels intersect at preferential locations along the separation channel are formed from a single co-planar, monolithic microfluidic device or microchip.

16. The apparatus of claim 1, wherein electrolyte contained in the first and the second electrolyte holders is electrically coupled to the pH gradient in the separation channel.

17. The apparatus of claim 16, wherein the first and second semi-permeable membranes are structured and arranged to electrically couple charged electrolyte contained in the first and the second electrolyte holders to the pH gradient in the separation channel and to prevent convection there between.

18. The apparatus of claim 17, wherein the first and second semi-permeable membranes are adapted to permit fluid within the separation channel to move bidirectionally over limited distances without affecting an acidic or substantially acidic nature of the fluid at the one of the sample inlet end and the outlet end and an alkaline or substantially alkaline nature of the fluid at the other of said sample inlet end and said outlet end.

* * * * *